United States Patent [19]

Allen et al.

[11] Patent Number: 4,899,581

[45] Date of Patent: Feb. 13, 1990

[54] METHOD AND APPARATUS FOR THE QUANTITATIVE MEASUREMENT OF ADHESION OF THIN FILMS

[75] Inventors: Mark G. Allen; Stephen D. Senturia, both of Boston, Mass.

[73] Assignee: Massachusetts Institute of Technology, Cambridge, Mass.

[21] Appl. No.: 351,330

[22] Filed: May 4, 1989

Related U.S. Application Data

[63] Continuation of Ser. No. 158,276, Feb. 19, 1988, abandoned.

[51] Int. Cl.$^4$ .................. G01N 19/04; G01N 3/10
[52] U.S. Cl. .................................................. 73/150 A
[58] Field of Search .............................. 73/150 A, 827

[56] References Cited

U.S. PATENT DOCUMENTS 4,501,154  2/1985  Mori ........................................ 73/827
4,612,805  9/1986  Bruce et al. ......................... 73/150 A

FOREIGN PATENT DOCUMENTS 29792    3/1977   Japan ..................................... 73/827
974224  11/1982  U.S.S.R. ............................. 73/150 A
974226  11/1982  U.S.S.R. ............................. 73/150 A
1455534 11/1976  United Kingdom ............. 73/150 A

OTHER PUBLICATIONS

J. W. Beams, "Mechanical Properties of Thin Films of Gold and Silver", *Structure and Properties of Thin Films*, editors: D. A. Neugebauer, J. B. Newkirk, D. A. Vermilyea; John Wiley & Sons, New York, (1959), pp. 183-192.

*Primary Examiner*—William A. Cuchlinski, Jr.
*Assistant Examiner*—W. Morris Worth
*Attorney, Agent, or Firm*—Hamilton, Brook, Smith & Reynolds

[57] ABSTRACT

A device for quantitatively measuring adherence of thin films provides a first substrate having an upper surface and a second substrate having a surface coplanar therewith. The second substrate is spaced on all sides from the first substrate by a cavity. The thin film is suspended over the cavity and adhered to the surfaces of the two substrates. A characteristic length of the area of the surface of the second substrate to which the film is adhered is made small relative to the characteristic length of the cavity. A pressure differential is applied across the thickness of the film such that the film debonds from the surface of the second substrate. Mechanical characteristics of the debonding of the film are observed and measured. The characteristics are thereafter related to provide a quantitative measurement of adherence of the thin film to the second substrate. A measurement of relative adherence between different films is obtained by testing a multilayered film structure. Other layers of various materials may be used to define a smaller area of adherence to which the film may be adhered.

15 Claims, 6 Drawing Sheets

METHOD AND APPARATUS FOR THE QUANTITATIVE MEASUREMENT OF ADHESION OF THIN FILMS

This is a continuation of co-pending application Ser. No. 07/158,276 filed on Feb. 19, 1988 now abandoned.

BACKGROUND OF THE INVENTION

Many methods exist for quantitatively measuring the adhesion of thin and/or well adhered films on various substrates. One conventional method involves peeling strips of the film off the substrate and measuring the force necessary to sustain this peel. In a closely related method known as the blister test, pressure is applied to a portion of the film suspended over a hole in the substrate until the film debonds or "blisters" from the substrate. The work of adhesion is then calculated from either the measured pressure at which peel/blister initiates or the "Pressure-Volume" work necessary to debond the film. These methods, however, are limited by the tensile strength of the film. In other words, if the films are very thin (or adhere very well), they will tear before peeling or blistering from the substrate.

There are some methods to overcome the limitation due to tensile strength of the film. One is to apply a backing layer to the thin film, allowing greater pressures to be sustained before rupture. This method has the disadvantage of possibly modifying the film's mechanical response or the film itself. Another method constrains the overall strain of a pressurized blister structure by placing a plate over the blister structure, also allowing larger pressures to be applied without rupture. Although this method will prevent strain induced rupture at the center of the blister, rupture at the edge of the blister and rupture due to defects in the film may still occur.

Accordingly, an adhesion test which allows the peeling of well adhered thin films at low pressures that avoid rupture is needed. Of particular interest is such testing of paints and coatings.

SUMMARY OF THE INVENTION

The disclosed method and apparatus allows peel of well adhered thin films at low pressures to quantitatively measure the adhesion of the films on various substrates. A structure is fabricated in which a film of interest is adhered to a top surface of a first substrate and is suspended over a hole in a central part of the substrate. A second substrate (referred to as an island substrate) is positioned within the hole and is spaced apart on all sides from the edges of the first substrate which form the hole. A portion of film which is suspended over the hole engages with a top surface of the island substrate. Preferably the top surfaces of the first and island substrates are coplanar. Bottom surfaces of the first substrate and the island substrate are fastened down to a rigid plate and the film is pressurized until it peels off the top surface of the island substrate. The pressure at which the film peels is measured and used to determine the work per unit surface area needed to debond the film from the island substrate, hereinafter referred to as the "work of adhesion" of the film, through the relationship $$\gamma_a = \frac{p_c^2 \, a_1^2}{32 \, \sigma_0 \, t} \left[ \frac{B^2 - 1}{\ln B} - 2 \right]^2 \qquad \text{Equation 1}$$

where
- $\gamma_a$ is work of adhesion of the film;
- $p_c$ is pressure to initiate peel;
- $2a_1$ is a characteristic length of the area to which the film is adhered;
- $2a_2$ is a characteristic length of the cavity;
- $B = a_2/a_1$;
- $\sigma_o$ is residual stress of the film; and
- $t$ is thickness of the film.

Equation 1 is an elementary relationship and is valid mainly for relatively high stress levels in which the effect of stretching the film is negligible compared to the bending against the residual stress. Other more elaborate equations may be similarly used instead of Equation 1 for a more precise determination of work of adhesion at other levels of stress.

Peel can be initiated at any conveniently low pressure by making the area of the top surface of the island substrate to which the film adheres sufficiently small relative to the hole in the substrate, i.e. making the quantity B large. Thus, the tensile strength limit of the film is overcome geometrically instead of by modifying the film (backing layer) or constraining a blister of the film (constrained blister test).

In one embodiment, the first and island substrates are monolithically fabricated by micromachining techniques. However, the two substrates may be fabricated of different materials. Pressurization of the film, and more specifically, applying a pressure differential across the thickness of the film may be accomplished by providing pressurizing fluids to the hole or by vacuum schemes and the like known in the art. The pressure at which the film peels and other mechanical properties exhibited by the film during peeling may be measured by a pressure transducer, optical means and/or other measuring means.

In an alternative embodiment, a middle layer may be deposited over the top surface of the island substrate. The middle layer may also be deposited over the top surface of the first substrate as well but is not suspended over the hole. The middle layer is chosen such that it adheres well to the island substrate relative to the adherence between the middle layer and the film of interest. The film of interest is positioned over the middle layer on the island (and first) substrate and is suspended over the hole. A pressure differential is applied across the film and mechanical properties are measured as in the previous embodiment. The film peels off the middle layer deposited on the island substrate before the middle layer debonds from the top surface of the island substrate due to the strong adherence of the middle layer to the island substrate. Examples of materials for the middle layer are silicon dioxide, polymers, aluminum, or other metals, where the film is polyimide and the island substrate is silicon.

In some cases, the area of adherence of the top surface of the island substrate required to initiate peel without rupture may be so small that the island substrate can no longer be conveniently fastened to the rigid plate before pressurization. In these cases, an adherend is deposited on a portion of the top surface of the island substrate. Then, a layer of material to which the film has poor adhesion is deposited over the adherend and remaining portion of the island substrate top surface. Using photolithographic techniques, an opening is cut in this poor adhesion or "release" layer. The size of this opening, which can be as small as a few microns, defines the area to which the subject film will be adhered to the adherend. The film is then deposited over the entire structure. Upon pressurization of the structure, the film easily peels off the release layer and stops when it reaches the small area of adherend exposed through the opening. The film can then be pressurized, peeled and measured in the previously stated manner. Copper is an example of a material suitable for the release layer when the film is polyimide. A polymer release layer is also suitable for certain applications.

In the case where the film forms a strong bond with the release layer and most other materials, an alternative release layer embodiment is used. In the alternative release layer embodiment, a second release layer is positioned on top of the original release layer. A hole is cut through both release layers to the adherend. The film is deposited over the entire structure. Upon pressurization of the structure, the interface between the two release layers fails which in turn allows the film and second release layer together to peel off the original release layer up to the area where the film is directly bonded to the adherend. The film is then further pressurized, peeled and measured to provide a quantitative measurement of the work of adhesion as in the foregoing embodiments. Examples of materials suitable for the alternative release layer embodiment are oxidized titanium for the original release layer, copper for the second release material and polyimide for the film, or polymer for both release layers. An equivalent effect of the alternative release layer can also be achieved by use of a single material, in place of the two release layers, which is able to easily fail cohesively.

In another embodiment of the present invention, the strength of adhesion between two films relative to that between two different films, or a common film and a different film, may be tested. A first film is deposited over the top surfaces of the first and island substrate but is not suspended over the hole. A second film is deposited over the first film, and a third film is deposited over the second film. The third film is suspended over the hole and pressurized. In the case where the second film is also suspended over the hole, a measurement of relative strengths of adherence between the island substrate-first film interface and the first film-second film interface may be made by visual observation during pressurization of the second and third films. The interface at which debonding occurs first is the interface of weaker adherence. In a second case where the second film is not suspended over the hole, a measurement of relative strengths of adherence between the island substrate-first film interface, first film-second film interface and second film-third film interface may be made in a similar manner. In both cases, it is exemplary that the first and third films are polyimide and that the second film is metallic. In addition, a quantitative measurement of the work of adhesion of the weakest film may be made in the manner described in the other disclosed embodiments.

Generally, the thickness of the test film is about 1 micron to about 100 microns in the foregoing embodiments. The test film may be a polymer.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
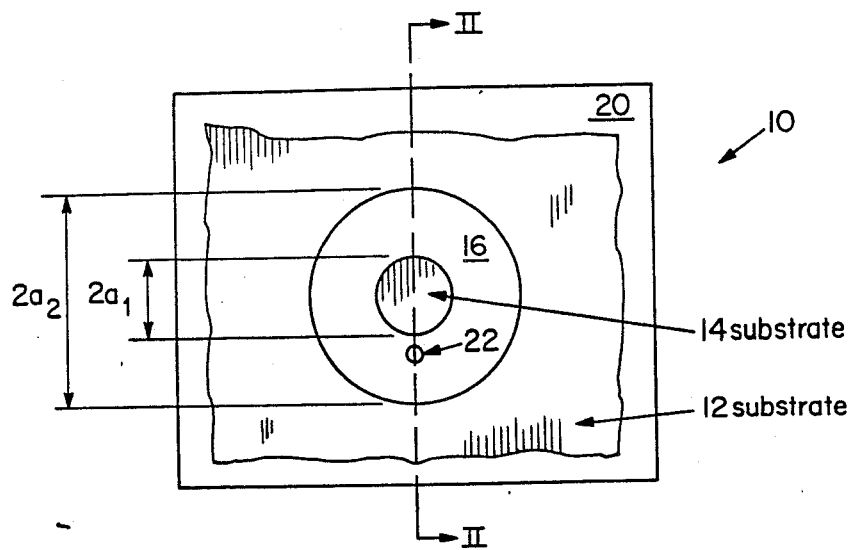
FIG. 1 is a plan view of a basic embodiment of the present invention.

The present invention provides a method and apparatus for quantitatively measuring the adhesion of thin and/or well adhered films (e.g. polymers, polyimide, and the like). In order to more fully appreciate the present invention, a review of the fundamental problem with the conventional blister test precedes the description of various embodiments of the invention and the general fabrication of those embodiments.

In the conventional blister test, a film of interest is suspended over a hole in a substrate. Fluid (gas or liquid) generated pressure is applied through the hole to the underside of the film and causes the suspended portion of film to deform and rise above the hole in the shape of a bubble. The blister test attempts to increase the amount of mechanical energy stored in the film during the process of deformation of the film (hereinafter, the film energy) to a sufficiently high level such that the energy which is required to induce an incremental debonding of the film from the substrate (hereinafter, the adhesive energy) is provided from the film energy. Such a situation results in the blistering or peeling of the film off the substrate in a direction radially outward from the outer edges of the hole. The amount of stored film energy is a function of pressure and volume of the bubble which is a function of the radius of the hole in the substrate. Hence, the amount of stored film energy may be increased by increasing the amount of applied pressure or by increasing the radius of the hole. However, at certain high pressures the film energy surpasses the level at which the film fractures (hereinafter, the tensile strength limit of the film) which results in an unsuccessful test due to the film tearing or the bubble rupturing before the film peels from the substrate.

Thus, an increase in radius of the hole has been used to increase the stored film energy to an amount larger than that needed to supply the adhesive energy while applying acceptable levels of pressure. However, the total adhesive energy increases with an increase in hole radius so that increasing the film energy within the bubble by increasing the hole radius also increases the total adhesive energy. As a result, the film energy never achieves the level necessary to supply the energy required for film debonding (i.e. the adhesive energy). On the other hand, total adhesive energy is related inversely to hole radius. Thus, at lower pressures very small hole radii are desired. However, a smaller hole radius results in a smaller bubble volume and thus a smaller possible amount of film energy within the bubble.

Thus, no adjustment of pressure and/or hole radius allows the film energy within the bubble to achieve the necessary total adhesive energy to sustain peeling of thin (and/or well-adhering) films without surpassing the tensile strength limit of the film. A mathematical discussion of the foregoing fundamental problem with the blister test for thin films and theoretical basis for the present invention is given in "Microfabricated Structures for the Measurement of Adhesion and Mechanical Properties of Polymer Films" by Mark G. Allen and Stephen D. Senturia, *Polymeric Materials: Science and Engineering*, Division of American Chemistry Society, Vol. 56, pages 735–739 (April 1987); and in "Analysis of Critical Debonding Pressures of Stressed Thin Films in the Blister Test" by Mark G. Allen and Stephen D. Senturia (submitted to *Journal of Adhesion* for Publication 1987). The foregoing articles are herein incorporated by reference.

In the present invention, the amount of adhesive energy is minimized so that the amount of film energy stored within the deformed film is able to be made greater than or equal to that needed to supply the adhesive energy without exceeding the tensile strength limit of the film. In addition, the present invention introduces a test structure which makes adhesive energy dependent on a radius of an isolated area to which the film adheres, and film energy dependent on the difference between the radius of a substrate hole which surrounds the isolated area and the radius of the isolated area. Thus, larger amounts of film energy may be achieved to measure larger levels of adhesive energy at acceptable (i.e. low) pressures and various hole radii.

This is accomplished by suspending the film of interest over a hole in a substrate, in the center of which exists an island of the substrate. The film is adhered to an upper surface of the substrate around the hole and an upper surface of the small island within the hole. A pressure differential is applied to the film structure until the film peels off the island. Based on linear fracture mechanics, the pressure level at which the film peels off the island is necessarily less than the pressure level at which film blisters radially out from the circumference of the hole. The amount of film energy can be maintained at a sufficiently high level by keeping the difference between hole radius and radius of the area on the island to which the film adheres, $(a_2-a_1)$, large while the adhesive energy is made small by making $a_1$, the radius of the adhered area, small. Thus, a decrease in the radius of the adhered island area reduces the pressure level at which peel occurs as illustrated through Equation 1 and fully discussed in the incorporated references. The pressure at which the film peels off the island is measured and related to a measured radius of the area of the film adhered to the island. The pressure-radius relationship is then used to determine the work of adhesion $\gamma_a$ of the film to the substrate as discussed in detail later. The film structure thus geometrically overcomes the tensile strength limitation of the film and the inherent problems of the conventional blister test.

Figure 2:
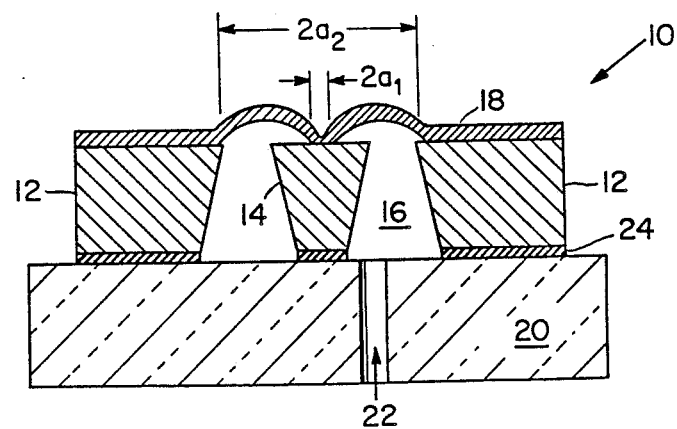
FIG. 2 is a cross-section through line II—II of the embodiment of FIG. 1.

FIG. 1 shows a plan view with the subject film removed and FIG. 2 shows a cross-section of an exemplary film structure of the present invention. The film structure 10 provides a major substrate 12 with a hole 16 and an island substrate 14 in the center of the hole 16. The hole 16 separates the island substrate 14 on all sides from the substrate 12. A membrane 18 of the film of interest is suspended over the hole 16 and adhered to the top surfaces of the substrate 12 and island 14. The island 14 and substrate 12 are fabricated of the same or different materials. The shape of hole 16 and island 14 may be circular or square or of any other regular geometrical shape. The hole 16 has a characteristic length (i.e. diameter or side) of $2a_2$, and the portion of the top surface area of the island 14 to which the film 18 adheres has a characteristic length of $2a_1$ as illustrated in FIG. 2.

The bottom surfaces of island 14 and the substrate 12, opposite their respective top surfaces, are fastened to a rigid plate 20, for example by an adhesive 24. Pressure is applied through a bore or pressure inlet 22 in plate 20. Alternatively, the structure fastened to a rigid plate without an inlet bore is placed in a vacuum chuck which permits the application of a pressure differential across the topside and underside of film 18.

Figure 7:
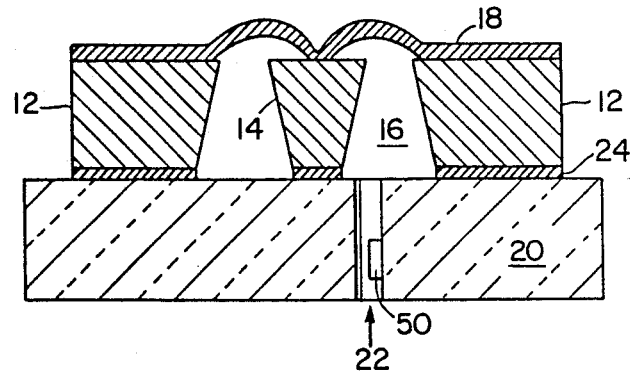
FIG. 7 is a schematic view of the embodiment of FIG. 1 with a pressure transducer for measuring applied pressure.
Figure 8:
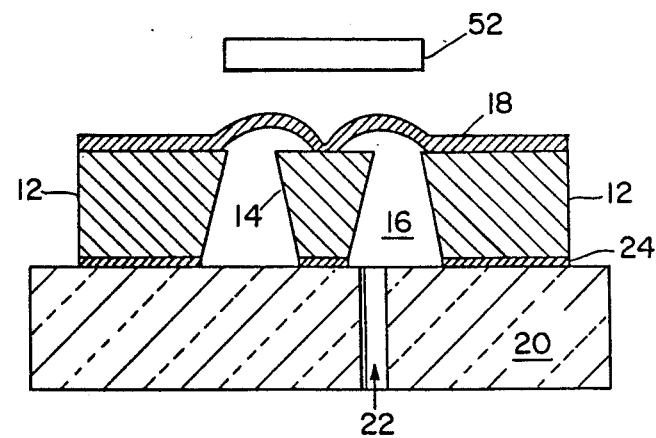
FIG. 8 is a schematic view of the embodiment of FIG. 1 with optical means for measuring peeling of a test film.

Film peeling now occurs only off the island 14. The pressure necessary to initiate and sustain peeling is measured by an attached pressure transducer 50 or by other known means as shown in FIG. 7. Incremental peel measurements are obtained by measuring pressure per change in amount of film 18 adhered to island 14 through a microscope 52 or by other commonly known methods as shown in FIG. 8.

Once the film has peeled entirely off the island 14 then the film becomes a suspended membrane from which other mechanical and elastic properties (i.e. residual stress) of the film may be determined in-situ by a measurement of load-deflection characteristics of the membrane as known in the art. For example, see J. W. Beams, "Mechanical Properties of Thin Films of Gold and Silver", *Structure of Properties of Thin Films*, John Wiley and Sons, New York 1959, pages 183–192. The work of adhesion of the film is then determined from a combination of the obtained island peel and load-deflection measurements in the following manner.

The island blister structure is modelled using an energy minimization approach combined with linear elastic fracture mechanics. Modelling the island structure as a circular adhered film membrane on an island at the center of a circular suspended membrane, the pressure to initiate peel ($p_c$), the work of adhesion ($\gamma_a$), and the radius of film still adhered to the island ($a_1$) are related on an elementary basis by:

$$\gamma_a = \frac{p_c^2 a_1^2}{32\sigma_0 t} f(B) \qquad (1)$$

where t is the film thickness, $a_2$ is the radius of the suspended film, $\sigma_o$ is the residual stress in the film, B is the ratio $a_2/a_1$, and f(B) is a function given by:

$$f(B) = \left[ \frac{B^2 - 1}{\ln B} - 2 \right]^2 \quad (2)$$

It is noted that the foregoing is an elementary relationship and that more elaborate relationships may be mode appropriate and/or suitable. The measured data relating pressure $p_c$ to the radius $a_1$ of the adhered island area are plotted in the form $a_1^2 f(B)$ vs. $p_c^{-2}$ in accordance with Equation 1. The slope of the best-fit line of the plotted points is proportional to the product of film residual stress, thickness and work of adhesion. The film residual stress is one of the measured properties and t is known, hence the proportionality can be solved for work of adhesion.

The foregoing film structure 10 embodying the present invention shows that the pressure necessary to initiate peel of well adhered/thin films can be made low enough that the tensile strength of the film is not exceeded simply by making the adherence area of island substrate 14 sufficiently small relative to the hole 16 in substrate 12. Thus, the tensile strength limit of the film is overcome geometrically. Further, the film structure does not suffer from the drawbacks of the constrained blister test in that relatively low pressures are used to initiate and sustain peel; therefore, the issues of stress concentration and defect failure are not important. In particular, film structure 10 can be used for the measurement of thin polyimide films of good adhesion.

Figure 3:
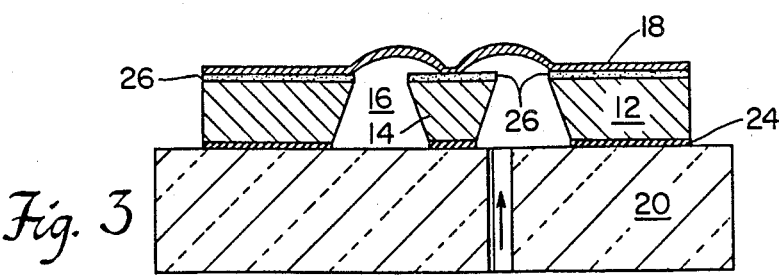
FIG. 3 is a cross-section of another embodiment of the invention which includes an island adherend.

In an alternative film structure shown in FIG. 3, the entire top surfaces of island 14 and substrate 12 are covered with an island adherend layer 26 which is of a different material than the island 14. The film 18 of interest is deposited over the island adherend layer 26 on the substrate 12 and island 14, and is suspended over hole 16. The structure is tested as in the above described film structure 10. In this case, the island adherend 26 is chosen to consist of a material which bonds very well to the island 14 so that the adherence between the subject film 18 and island adherend 26 is weaker than the adherence between the island adherend 26 and island 14. As a result, the subject film 18 peels off from the island adherend 26 before the island adherend debonds from island 14. This film structure is suitable for testing the adherence of, for example, polyimide (as the subject film) to silicon dioxide, aluminum, copper or polymers (as the island adherend) where the island is silicon.

In order for the film structures of the present invention to be generally applicable, it is necessary to make the pertinent surface of the island arbitrarily small. However, the island must not be so small that it cannot be fastened down to the rigid plate 20. In other words, while it may be necessary for the island to be microscopic in size so that the tensile strength of the film will not be exceeded in measuring adhesion, it is necessary for the island to be macroscopic in size in order that it be fastened down prior to measurement.

Figure 4A:
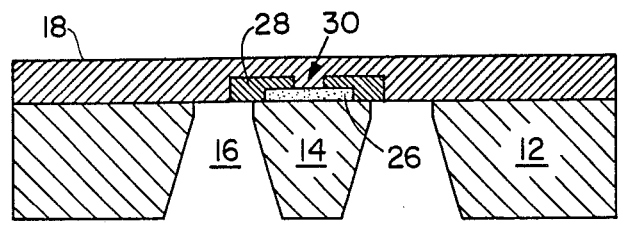
FIGS. 4a and 4b are cross-sections of third and fourth embodiments of the present invention with only a portion of an island adherend pad exposed to a test film.
Figure 4B:
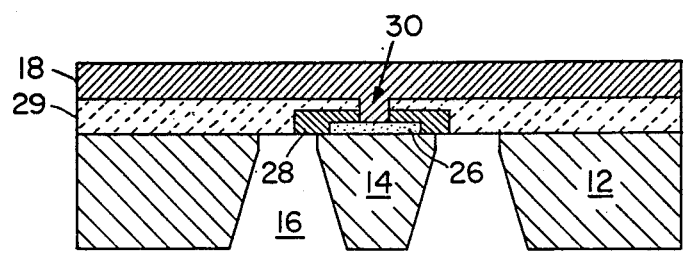

As illustrated in FIGS. 4a and 4b, this problem is overcome by using a macroscopic island 14 and patterning a relatively smaller island adherend pad 26 on the top surface of the island. The entire top surface of island 14 is covered with a "release layer" 28 (or material to which the film 18 will not stick). Release layer 28 is sufficiently thin (about 100 Å to about 1000 Å) so that the mechanical behavior of the film 18 is not perturbed. In a central area of release layer 28 lies a microscopic opening 30 which allows the subject film 18 to see the adherend pad 26 on the island 14. The subject film 18 is deposited over the substrate 12, hole 16 and release layer 28 on island 14. Due to the release layer 28, only a small area of the film 18 actually adheres to the adherend pad 26 through opening 30 in the release layer 28. When a small pressure is applied, the film 18 will easily peel from the release layer 28 and stop when it reaches the exposed portion of adherend pad 26. Continued application of pressure, obtaining measurements and performing adhesion analysis is then as described previously. The characteristic length (i.e. diameter-if circular, or side-if square) of opening 30 defines a maximum initial $2a_1$ in Equation 1 and is, for example, in the range of about 1 micron to about 2 mm. Thus, a microscopic adhered area is achieved on a macroscopic island.

In the case where film 18 adheres or bonds extremely well to most any material of which the release layer 28 is composed, a combination of release layers as shown in FIG. 4b is used. In the structure of FIG. 4b, after the first release layer 28 is deposited and patterned over the adherend pad 26 and top surface of island 14, a second release layer 29 is deposited and patterned over the first release layer 28. The second release layer 29 may also be positioned on the top surface of substrate 12 and suspended over hole 16. Second release layer 29, like first release layer 28, is sufficiently thin such that the mechanical behavior of film 18 is not perturbed. In addition, the second release layer 29 adheres weakly to first release layer 28 forming a weaker bond than that formed between second release layer 29 and film 18. Opening 30 is made to continue through the second release layer 29 so as to expose a portion of the adherend pad 26 and define a maximum initial $2a_1$ in Equation 1. The subject film 18 is deposited over the second release layer 29 and adheres to the portion of adherend pad 26 exposed through opening 30. When a small pressure is applied, the film 18 and second release layer 29 adhered relatively well to each other peel as a unitary body from the first release layer 28 and stop when the exposed portion of the adherend pad 26 which is adhered to only film 18 is reached. A continued application of pressure, obtaining of measurements and performing of adhesion analysis is then as previously described. Again the characteristic length of opening 30 defines an initial value of $2a_1$ in Equation 1. Thus, a combination of release layers can be used in place of a single release layer when the film-release layer interface is strong. Release of the film from the first release layer is accomplished when there exists a failure between the first and second release layers. An equivalent effect can be obtained if the two release layers are a single material which can easily fail cohesively.

Figure 5A:
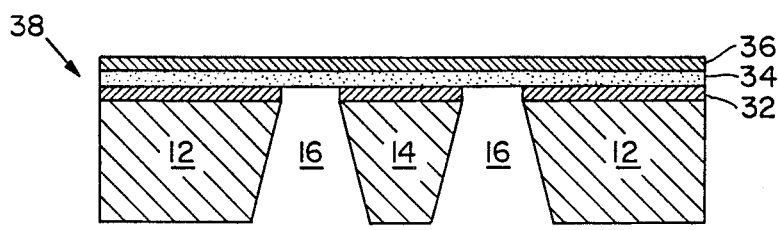
FIGS. 5a and 5b are cross-sections of embodiments of the present invention which provide relative adhesion measurements.

Another embodiment of the present invention provides a measurement of relative adhesion between various layers deposited over the island structure. An exemplary three level island structure 38 is provided in FIGS. 5a and 5b. In FIG. 5a, a first film 32 of interest is deposited over the top surfaces of the island 14 and substrate 12. The first film 32 is not suspended over hole 16 and leaves hole 16 accessible around island 14. A middle layer of material 34 is layered over the first film 32 and suspended over hole 16. A second film 36 of interest is layered over the total surface of the middle layer 34 and provides mechanical strength for layer 34. A pressure differential is applied to the layered structure 38 and produces stresses between the top surface of island 14 and first film 32 and between first film 32 and middle layer 34. The corners or edges where one layer adheres to another layer, become potential sites where peeling may occur under the applied pressure. Peeling begins at the weakest site and observance of such peeling provides a determination of relative strength of adhesion between the top surface of island 14, first film 32 and middle layer 34. That is, if first film 32 peels off from island 14 before first film 32 and middle layer 34 peel apart from each other then a stronger bond exists in the adherence between first film 32 and middle layer 34 than in the adherence between first film 32 and island 14. Conversely, if first film 32 and middle layer 34 peel apart before first film 32 peels away from island 14, then the adherence between island 14 and first film 32 is stronger than the adherence between first film 32 and middle layer 34. In addition, a quantitative measurement of the work of adhesion of the weakest adhered interface can be obtained by obtaining the measurements during pressurization and debonding of the film and by performing the analysis described in the previous embodiments.

Figure 5B:
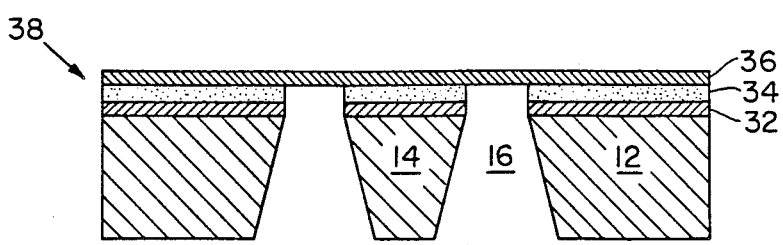

The three layered island structure 38 of FIG. 5a may be modified by the removal of that portion of middle layer 34 which is suspended over hole 16 as shown in FIG. 5b. In this arrangement, relative adhesion between the island 14, first film 32, middle layer 34 and second film 36 is tested. Second film 36 serves as a carrier of energy during the pressurization of the layered island structure. As in the structure of FIG. 5a, peeling will begin at the corner or edge of the weakest adhering interface between island 14 and first film 32, first film 32 and middle layer 34, and middle layer 34 and second film 36. Observation of such peeling is made by conventional means to provide an indication of relative adhesion. In addition, a quantitative measurement of the work of adhesion of the weakest adhered interface may be obtained as described above.

The foregoing layered island structures of FIGS. 5a and 5b are particularly suitable for testing relative adhesion between a metallic middle layer 34 and a first and second polyimide film 32 and 36. Further, by moving potential peel sites out of alignment with the corners or edges of island 14 (e.g. film layer 32 covering less than the entire top surface area of the island), the design geometry of the layered structure is modified to place the first film of interest at a site which peels first to test adherence between the film and one material (i.e. the island) relative to adherence between the film and another material (i.e. the middle layer). It is understood that various layering schemes may be achieved in light of the foregoing and that the foregoing is only an illustration and not limitation of the fundamental principles involved in a relative adhesion measurement device of the present invention.

Figure 6A:
FIGS. 6a–6p are schematic illustrations of the process for fabricating the disclosed embodiments of the invention.

The devices of the present invention are fabricated using micromachining techniques. One or several island test sites may be fabricated in one wafer. For simplicity, the following describes the fabrication of one island test site in a ½ mm thick (100) silicon wafer 40 shown in FIG. 6a. It is understood that other such island test sites may be similarly fabricated in the same or other wafers and that wafers of different material may be used.

Figure 6B:
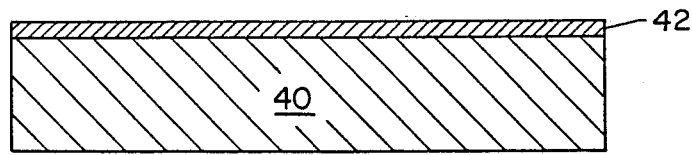
Figure 6C:
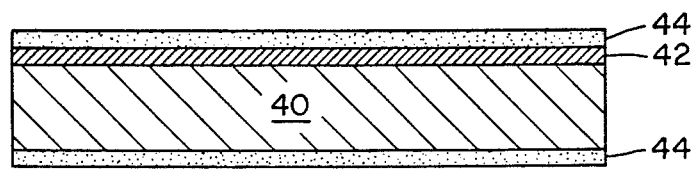

As shown in FIG. 6b, boron is diffused into one side of the silicon wafer 40 from a boron nitride or other known source at about 1175° C. to form a 5 micron thick p+etch stop 42 in the wafer 40. The wafer is then annealed in oxygen to provide 3000 Å thick SiO$_2$ etch masks 44 on each side of the wafer as shown in FIG. 6c.

Figure 6D:
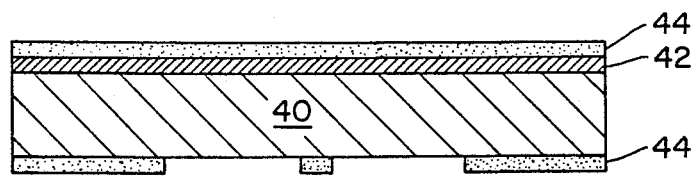

The hole 16 and island 14 are patterned by photolithographic techniques as illustrated in FIG. 6d. The characteristic length 2a$_2$ of hole 16 is about 2 mm to 2 cm and the characteristic length of island 14 is, for example, about 0.5 mm to about 5 mm. The wafer is placed in a 50% hydrazine in water solution to anisotropically etch the hole 16 around island 14 shown in FIG. 6e. The SiO$_2$ layers 44 are optionally stripped off with HF. The wafer is now in a form to which the film of interest and other layers may be applied as described in the foregoing embodiments.

For the device of FIGS. 1 and 2, the film 18 of interest is deposited over the top surface of wafer 40 in a thickness on the order of about 1 micron to about 100 microns by spin casting and curing. Other methods which do not rupture the p+boron diffusion layer 42 may be used to deposit the film of interest onto the wafer. The wafer 40 is then dry etched or SF$_6$ plasma etched from the backside to remove the p+silicon 42 about the outside edges of island 14 so that film layer 18 is freely suspended over hole 16 as shown in FIG. 6f. The backside of the wafer 40 is then attached (glued) to a base plate 20 with a bore 22 through the base plate in communication with the wafer hole 16 as shown and described in FIGS. 1 and 2.

In the device of FIG. 3, the desired island adherend 26 is applied to the top surface of wafer 40. For example, aluminum is evaporated on the top side of wafer 40 with the SiO$_2$ etch masks 44 removed as shown in FIG. 6g. The film of interest 18 is deposited over the island adherend layer 26. The p+layer 42 about the outer edges of island 14 are removed by dry etching or SF$_6$ plasma etching through the backside of wafer 40, and the adherend layer 26 suspended over hole 16 is removed by wet etching or plasma (dry) etching as shown in FIG. 6h.

Figure 6E:
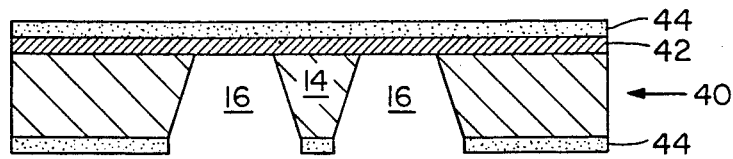
Figure 6F:
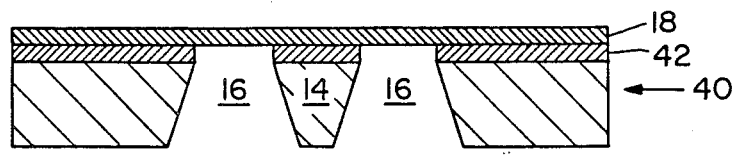
Figure 6G:
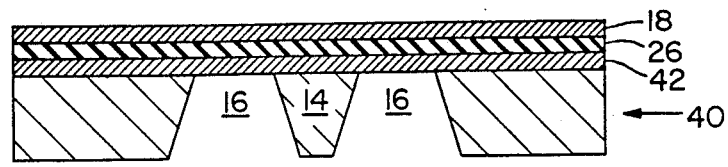
Figure 6H:
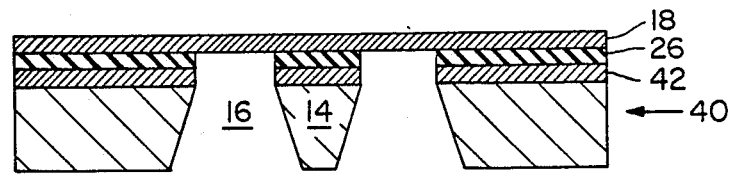
Figure 6I:
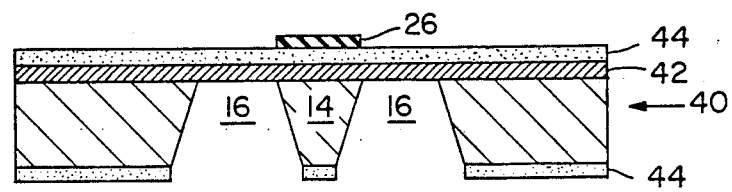
Figure 6J:
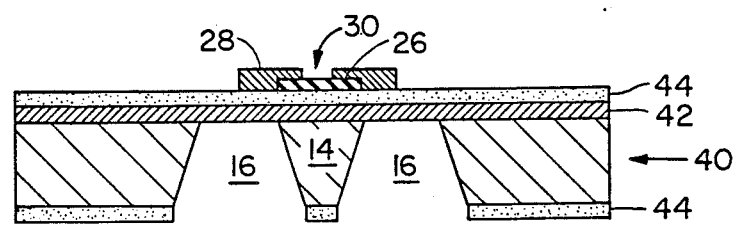
Figure 6K:
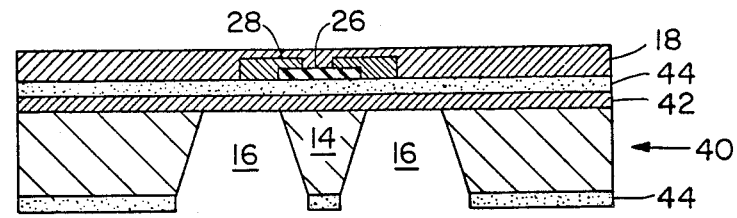
Figure 6L:
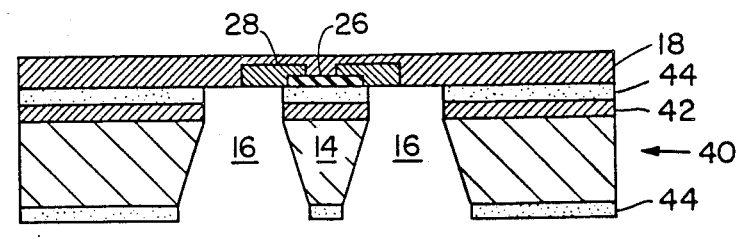

In the structure of FIG. 4a, a desired adherend pad 26 as thin as one layer of atoms thick is deposited and patterned over a portion of the top surface of island 14 as shown in FIG. 6i. A 100 Å to 150 Å thick film of copper serving as a release layer 28 is then deposited and patterned so as to expose only a small portion (about 1 micron to 200 microns on a side) of the adherend pad 26 through opening 30 as shown in FIG. 6j. Such patterning is preferably accomplished by photolithographic techniques. The release layer 28 may alternatively comprise, for example, a polymer. The film 18 of interest (e.g. polyimide) is then spin cast and cured on wafer 40 shown in FIG. 6k. The portions of the p+layer 42 and SiO$_2$ layer 44 surrounding island 14 are removed using a backside SF$_6$ plasma etch to form the desired suspended membrane for testing as shown in FIG. 6l.

Figure 6M:
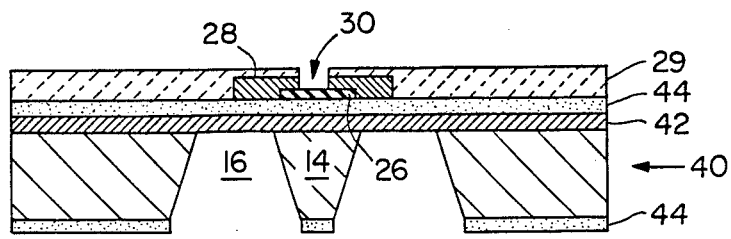
Figure 6N:
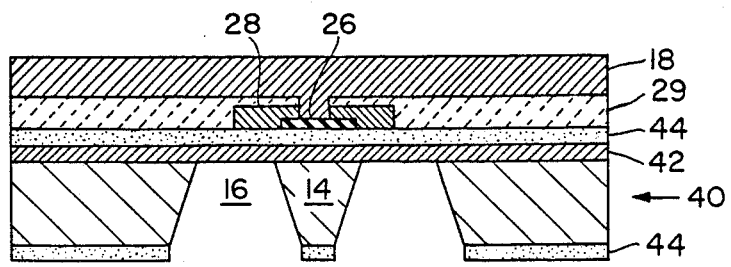
Figure 6O:
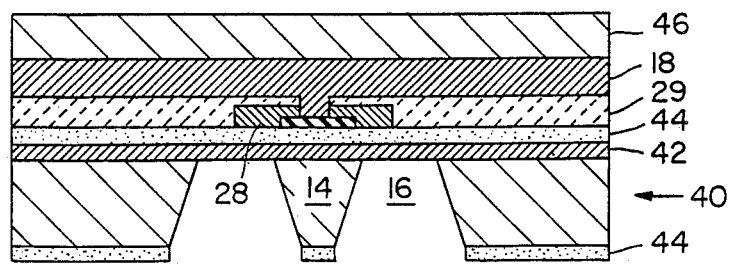
Figure 6P:
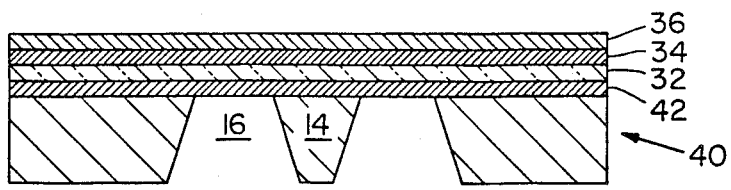

In the structure of FIG. 4b, fabrication through FIG. 6j is as described above for the structure of FIG. 4a except that release layer 28 is oxidized titanium. A second release layer 29 consisting of copper is then deposited and patterned over first release layer 28 with only a small portion of adherend pad 26 exposed through opening 30 as shown in FIG. 6m. Alternatively, the first and second release layers may comprise polymer. Film 18 (polyimide) is then spin cast and cured on second release layer 29 as shown in FIG. 6n. The portions of the p+layer 42 and SiO$_2$ layer 44 surrounding island 14 are removed as described above in FIG. 6l. Optionally, a backing layer 46 of polyimide for instance, may be deposited over film 18 before removal of the p+layer 42 and SiO$_2$ layer 44 as shown in FIG. 6o. The backing layer 46 provides support to film 18 when film 18 is not mechanically strong, for example a thin metal film subject to plastic deformation.

In the structures of FIGS. 5a and 5b, the prepared wafer 40 as shown in FIG. 6e is stripped of the SiO$_2$ layer 44 with HF. A first film 32 is spin cast and cured, or otherwise deposited, over the entire top surface of wafer 40. A middle layer 34 is deposited over the entire surface of the first film 32, and a second film layer 36 is deposited over the entire surface of the middle layer 34 as shown in FIG. 6m. The portions of the p+layer 42 and first film 32 which lie about island 14 are etched from the backside of wafer 40 through hole 16 to provide the structure of FIG. 5a. A different etchant is used to remove the portion of the middle layer 34 about island 14 through hole 16 to provide the structure of FIG. 5b in which the second film 36 is freely suspended over hole 16.

While the invention has been particularly shown and described with reference to a preferred embodiment thereof, it will be understood by those skilled in the art that various changes in form and details may be made therein without departing from the spirit and scope of the invention as defined by the appended claims.

We claim:

1. A device used in measuring adherence of a test film to a subject surface, comprising:
   a substrate surface for holding the test film thereon and having a cavity therethrough, the subject surface positioned in the cavity such that the substrate surface and the subject surface lie in a common plane, and in the plane the cavity surrounds the subject surface such that the subject surface is spaced apart from the substrate surface on all sides across the cavity; the film having one portion adhered to the substrate surface and a second portion suspended over the cavity, and a region of the suspended second portion of the film being adhered to the subject surface;
   means for applying a pressure differential across the suspended second portion of the film such that the film debonds from the subject surface;
   means for measuring residual stress of the film;
   means for measuring applied pressure differential at which debonding of the adhered region of the film is initiated; and
   means for measuring radius of the region of film adhered to the subject surface with respect to applied pressure; wherein said applied pressure differential, residual stress and radius measurement along with a measurement of film thickness are used to provide a quantitative measurement of adherence of the test film to the subject surface.

2. A device as claimed in claim 1 wherein the test film comprises a polymer.

3. A device as claimed in claim 2 wherein the test film comprises polyimide.

4. A device as claimed in claim 1 wherein the substrate surface and subject surface are monolithically formed by micromachining techniques.

5. A device as claimed in claim 1 wherein said means for applying a pressure differential includes a pressurizing fluid.

6. A device as claimed in claim 1 wherein said means for measuring applied pressure differential include a pressure transducer.

7. A device as claimed in claim 1 wherein said means for measuring radius include optical means.

8. A device as claimed in claim 1 wherein the measurements provide a quantitative measurement of adherence by being related to work of adhesion $\gamma_a$ by $$\gamma_a = \frac{p_c^2 a_1^2}{32\sigma_0 t} \left[ \frac{B^2 - 1}{\ln B} - 2 \right]^2$$

where
   $p_c$ is the pressure at which debonding of the suspended film is initiated;
   $2a_1$ is a characteristic length of the region of the film adhered to the subject surface;
   $2a_2$ is a characteristic length of the cavity;
   $B = a_2/a_1$;
   $\sigma_o$ is residual stress of the film; and
   t is thickness of the film.

9. A method of measuring adherence, the steps comprising:
   providing a cavity which separates on all sides a central portion of an upper planar surface of a substrate from a remaining portion of the surface;
   adhering a film of interest to the remaining and central portions of the surface in a manner such that a part of the film is suspended over the cavity;
   applying a pressure differential across the suspended part of the film to cause the film to debond from the central portion of the surface while adhering to the remaining portion of the surface;
   measuring applied pressure differential at which debonding is initiated;
   measuring mechanical properties including residual stress and thickness of the film under the applied pressure differential and radius of the film remaining on the central portion has been inserted; and
   utilizing the measured properties together with the measured pressure differential has to mathematically obtain a quantitative measurement of adherence between the film and substrate.

10. A method as claimed in claim 9 wherein the step of providing a cavity includes selective etching of portions of the substrate defined by photolithographic techniques.

11. A method as claimed in claim 9 wherein the step of utilizing the measured properties includes applying the relationship $$\gamma_a = \frac{p_c^2 a_1^2}{32\sigma_0 t} \left[ \frac{B - 1}{\ln B} - 2 \right]^2$$

where
   $\gamma_a$ is work of adhesion of the film;
   $p_c$ is the applied pressure differential at which debonding of film is initiated;
   $2a_1$ is a characteristic length of that portion of the central portion of the surface to which the film is adhered;
   $2a_2$ is a characteristic length of the hole;
   $B = a_2/a_1$;
   $\sigma_o$ is residual stress of the film; and
   t is thickness of the film.

12. A method of measuring adherence, the steps comprising:
   forming a first substrate having an upper planar surface;

forming a second substrate having a surface coplanar with the upper planar surface of the first substrate;

spacing the second substrate on all sides from the first substrate by a cavity;

suspending a film over the cavity, the film being adhered to the surfaces of the first and second substrates;

causing the film suspended over the cavity between the two surfaces to bulge upwardly and subsequently causing the film to debond from the surface of the second substrate;

measuring mechanical and elastic properties of the film during and after debonding of the film from the surface of the second substrate such as residual stress, pressure at which debonding is initiated, thickness of the film and radius of the film adhered to the second substrate surface; and computationally relating the mechanical properties of the film measured during and after debonding to provide a quantitative measurement of adherence of the film.

13. A method of fabricating a device for quantitatively measuring adherence of a test film, the steps comprising:

by micromachining techniques, forming with a substrate a first upper planar surface and a second sufficiently coplanar surface spaced on all sides from the first surface by a cavity; and adhering a test film to the first and second surfaces in a manner which suspends a part of the test film over the cavity such that application of a pressure differential across the suspended part of the test film causes bulging and subsequent debonding of the test film adhered to the second surface.

14. A device used in measuring adherence of a test film to a subject surface, comprising:

a substrate having a cavity which surrounds the subject surface such that the subject surface is spaced apart from the substrate on all sides, the film being adhered to the substrate and suspended over the cavity and a portion of the suspended film being adhered to the subject surface, the substrate and the subject surface monolithically formed by micromachining techniques;

means for applying a pressure differential across the suspended film such that the film debonds from the subject surface;

means for measuring applied pressure differential at which debonding of the film from the subject surface is initiated;

means for measuring stress of the film; and means for measuring radius of the portion of film adhered to the subject surface with respect to applied pressures, wherein said applied pressure differential, residual stress and radius measurement along with a measurement of film thickness are used to provide a quantitative measurement of adherence of the test film to the subject surface.

15. A device used in measuring adherence of a test film to a subject surface, comprising:

a substrate surface for holding the test film thereon and having a cavity therethrough, the subject surface positioned in the cavity such that the substrate surface and the subject surface lie in a common plane, and in the plane the cavity surrounds the subject surface such that the subject surface is spaced apart from the substrate surface on all sides across the cavity, the test film having one portion adhered to the substrate surface and a second portion suspended over the cavity, and a region of the suspended second portion of the test film being adhered to the subject surface;

means for applying a pressure differential across the suspended second portion of the test film such that the film debonds from the subject surface;

means for measuring applied pressure differential at which debonding of the adhered region of the test film is initiated; and means for measuring radius of the region of test film adhered to the subject surface with respect to applied pressure.

* * * * *